(12) United States Patent
Orinski

(10) Patent No.: US 8,250,745 B1
(45) Date of Patent: Aug. 28, 2012

(54) PROCESS FOR MANUFACTURING A MICROCIRCUIT COCHLEAR ELECTRODE ARRAY

(75) Inventor: William G. Orinski, Stevenson Ranch, CA (US)

(73) Assignee: Advanced Bionics, LLC, Valencia, CA (US)

( * ) Notice: Subject to any disclaimer, the term of this patent is extended or adjusted under 35 U.S.C. 154(b) by 565 days.

(21) Appl. No.: 12/338,758

(22) Filed: Dec. 18, 2008

Related U.S. Application Data

(60) Provisional application No. 61/023,389, filed on Jan. 24, 2008.

(51) Int. Cl.
*H05K 3/20* (2006.01)

(52) U.S. Cl. ............ 29/831; 29/592.1; 29/417; 29/595; 29/846; 29/854; 156/73.1; 347/54; 347/68; 347/69; 347/70; 427/79; 427/80

(58) Field of Classification Search .................... 29/417, 29/592.1, 595, 831, 846, 854; 156/73.1; 347/54, 68–72; 361/283, 301; 427/79, 80
See application file for complete search history.

(56) References Cited

U.S. PATENT DOCUMENTS

| | | | |
|---|---|---|---|
| 4,031,310 A | 6/1977 | Jachimowicz | |
| 4,261,372 A | 4/1981 | Hansen et al. | |
| 4,284,085 A | 8/1981 | Hansen et al. | |
| 4,762,135 A | 8/1988 | van der Puije et al. | |
| 4,832,051 A | 5/1989 | Jarvik et al. | |
| 5,580,699 A | 12/1996 | Layman et al. | |
| 5,658,709 A | 8/1997 | Layman et al. | |
| 5,720,099 A | 2/1998 | Parker et al. | |
| 5,987,361 A | 11/1999 | Mortimer | |
| 6,309,410 B1 * | 10/2001 | Kuzma et al. | 607/137 |
| 6,355,401 B1 | 3/2002 | Graves et al. | |
| 6,374,143 B1 | 4/2002 | Berrang et al. | |

(Continued)

FOREIGN PATENT DOCUMENTS

AU 2004000903484 6/2004

(Continued)

OTHER PUBLICATIONS

Rodger et al., Flexible parylene-based multielectrode array technology for high-density neural stimulation and recording, Sensors and Actuators B 132 (2008) 449-460.

(Continued)

*Primary Examiner* — Paul D Kim
(74) *Attorney, Agent, or Firm* — Steven L. Nichols; VanCott, Bagley, Cornwall & McCarthy P.C.

(57) ABSTRACT

A process for manufacturing a single microcircuit into an integrated cochlear electrode array includes securing and supporting a nonconductive film substrate; attaching a metallic ribbon to a surface of the substrate; machining a flat multiconductor microcircuit from the ribbon to produce a flat elongated multiconductor tail portion with spaced outwardly exposed electrode receiving pads, and a flat multiconductor head portion connected to the tail portion and having spaced outwardly exposed attachment pads; laminating the flat microcircuit between the film substrate and an insulating cover; excising the laminated microcircuit from the film substrate with the electrode receiving pads exposed; wrapping the tail portion of the excised laminated microcircuit into a helix with the exposed electrode receiving pads wrapped around the insulating cover; mounting and electrically connecting the ring electrodes on and to the exposed electrode pads; and overmolding the helix tail portion with a polymeric material to ready the microcircuit for cochlear implant.

10 Claims, 17 Drawing Sheets

U.S. PATENT DOCUMENTS

| | | | |
|---|---|---|---|
| 6,421,569 B1 * | 7/2002 | Treaba et al. | 607/137 |
| 6,643,552 B2 | 11/2003 | Edell et al. | |
| 6,678,564 B2 | 1/2004 | Ketterl et al. | |
| 6,757,970 B1 | 7/2004 | Kuzma et al. | |
| 6,779,257 B2 | 8/2004 | Kiepen et al. | |
| 6,782,619 B2 | 8/2004 | Corbett et al. | |
| 6,843,870 B1 | 1/2005 | Bluger | |
| 6,974,533 B2 | 12/2005 | Zhou | |
| 7,047,081 B2 | 5/2006 | Kuzma | |
| 7,067,765 B2 | 6/2006 | Bauer et al. | |
| 7,085,605 B2 | 8/2006 | Bluger et al. | |
| 7,142,909 B2 | 11/2006 | Greenberg et al. | |
| 7,240,416 B2 | 7/2007 | Milojevic et al. | |
| 7,326,649 B2 | 2/2008 | Rodger et al. | |
| 7,406,352 B2 | 7/2008 | Gibson | |
| 7,587,248 B2 | 9/2009 | Risi et al. | |
| 7,774,071 B2 | 8/2010 | Schuller | |
| 7,970,481 B2 | 6/2011 | Milojevic | |
| 2003/0097165 A1 | 5/2003 | Krulevitch et al. | |
| 2003/0236562 A1 | 12/2003 | Kuzma | |
| 2004/0015221 A1 | 1/2004 | Kuzma | |
| 2004/0020686 A1 | 2/2004 | Alfonso Perez et al. | |
| 2004/0147825 A1 | 7/2004 | Milojevic et al. | |
| 2004/0147992 A1 | 7/2004 | Bluger et al. | |
| 2004/0172118 A1 | 9/2004 | Gibson | |
| 2004/0256146 A1 | 12/2004 | Frericks et al. | |
| 2005/0016657 A1 | 1/2005 | Bluger | |
| 2005/0107858 A1 | 5/2005 | Bluger | |
| 2005/0256561 A1 | 11/2005 | Gantz et al. | |
| 2006/0003090 A1 | 1/2006 | Rodger | |
| 2006/0089700 A1 | 4/2006 | Darley | |
| 2006/0095105 A1 | 5/2006 | Jog et al. | |
| 2006/0206185 A1 | 9/2006 | Schuller | |
| 2006/0236532 A1 | 10/2006 | Schuller | |
| 2006/0247754 A1 | 11/2006 | Greenberg et al. | |
| 2006/0255293 A1 | 11/2006 | Tai et al. | |
| 2006/0259112 A1 | 11/2006 | Greenberg et al. | |
| 2007/0123963 A1 | 5/2007 | Krulevitch | |
| 2007/0168004 A1 | 7/2007 | Walter | |
| 2007/0293749 A1 | 12/2007 | Zhou et al. | |
| 2008/0027525 A1 | 1/2008 | Frericks | |
| 2008/0044591 A1 | 2/2008 | Laude | |
| 2008/0140156 A1 | 6/2008 | Rodriguez et al. | |
| 2008/0262584 A1 | 10/2008 | Bottomley et al. | |
| 2009/0043358 A1 | 2/2009 | Dadd et al. | |
| 2009/0143848 A1 | 6/2009 | Greenberg et al. | |
| 2009/0165921 A1 | 7/2009 | Kaiser | |
| 2009/0229739 A1 | 9/2009 | Schuller | |
| 2010/0023102 A1 | 1/2010 | Spruit | |
| 2010/0287762 A1 | 11/2010 | Milojevic et al. | |
| 2010/0305673 A1 | 12/2010 | Jolly | |
| 2011/0098719 A1 | 4/2011 | Llinas | |
| 2011/0180305 A1 | 7/2011 | Johnson | |
| 2012/0004715 A1 | 1/2012 | Ramachandran et al. | |

FOREIGN PATENT DOCUMENTS

| | | |
|---|---|---|
| EP | 0002068 A2 | 5/1979 |
| EP | 0007157 A2 | 1/1980 |
| EP | 0007157 A3 | 8/1980 |
| EP | 1574181 A1 | 9/2005 |
| EP | 0888701 B1 | 10/2007 |
| EP | 2046443 A1 | 4/2009 |
| EP | 2066397 B1 | 2/2010 |
| EP | 1587454 B1 | 4/2010 |
| EP | 1574181 B1 | 10/2010 |
| EP | 2286871 A2 | 2/2011 |
| EP | 2298408 A2 | 3/2011 |
| EP | 1651305 B1 | 8/2011 |
| WO | 9706760 A1 | 2/1997 |
| WO | 9728668 A1 | 8/1997 |
| WO | 02078575 A1 | 10/2002 |
| WO | 02089907 A1 | 11/2002 |
| WO | 03017329 A2 | 2/2003 |
| WO | 03017329 A3 | 2/2003 |
| WO | 03049638 A2 | 6/2003 |
| WO | 03049638 A3 | 6/2003 |
| WO | 03090848 A1 | 11/2003 |
| WO | 2004035133 A1 | 4/2004 |
| WO | 2004054474 A1 | 7/2004 |
| WO | 2004064687 A1 | 8/2004 |
| WO | 2005004978 A1 | 1/2005 |
| WO | 2006000031 A1 | 1/2006 |
| WO | 2007065216 A2 | 6/2007 |
| WO | 2007065216 A3 | 6/2007 |
| WO | 2008011721 A1 | 1/2008 |
| WO | 2008031144 A1 | 3/2008 |
| WO | 2009062114 A2 | 5/2009 |
| WO | 2009062114 A3 | 5/2009 |
| WO | 2009065127 A1 | 5/2009 |
| WO | 2009065171 A1 | 5/2009 |
| WO | 2010055421 A1 | 5/2010 |
| WO | 2010079875 A1 | 7/2010 |
| WO | 2010138567 A2 | 12/2010 |
| WO | 2012003295 A1 | 1/2012 |
| WO | 2012003297 A1 | 1/2012 |

OTHER PUBLICATIONS

Henle et al, Scaling Limitations of Laser-Fabricated Nerve Electrode Arrays; 30th Annual International IEEE EMBS Conference; Aug. 20-24, 2008; pp. 4208-4211; Vancouver, British Columbia, Canada.

Schuettler et al, Fabrication of Implantable Microelectrode Arrays by Laser Cutting of Silicone Rubber and Platinum Foil, Institute of Physics Publishing; Journal of Neural Engineering; Feb. 22, 2005, pp. 5121-5128; United Kingdom.

Schuettler et al, Fabricating microelectrode arrays by laser-cutting of platinum foil and silicone rubber, 9th Annual conference of the International FES Society, Sep. 2004, pp. 1-3, Bournemouth, UK.

* cited by examiner

PROCESS FOR MANUFACTURING A MICROCIRCUIT COCHLEAR ELECTRODE ARRAY

RELATED PATENT APPLICATION

The present invention claims the benefit of U.S. Provisional Patent Application Ser. No. 61/023,389 filed Jan. 24, 2008, which is incorporated herein by reference.

BACKGROUND OF INVENTION

Current procedures for manufacturing cochlear electrodes involve operator intervention throughout much of the manufacturing process wherein the electrodes are manually formed and handled. This results in relatively slow processing of the electrodes and subjects the electrodes to undesired mechanical stresses and breakage.

It is an object of the present invention to provide a more compact and robust cochlear electrode design and a more rapid process of manufacture that reduces operator intervention, reduces material waste and rework of the electrodes and increases the throughput and efficiency of electrode manufacture.

SUMMARY OF INVENTION

The present invention is directed to a microcircuit integrated cochlear electrode array and a process for manufacturing the electrode.

Basically, the microcircuit comprises flat multiconductor head and tail portions. The multiconductor head portion has spaced outwardly exposed circuit attachment pads. The flat multiconductor tail portion is helically wrapped with spaced electrode attachment pads on an exposed outer surface thereof. Ring electrodes are carried by the helically wrapped tail portion and extend around and are electrically connected to the electrode receiving pads and overmolded with a suitable polymeric material. Further, the tail and head portions preferably are laminated between a nonconductive film substrate and an insulating cover and a portion of the tail portion is unwrapped to define a lateral offset forming a stylet receiving lumen for a balance of the helically wrapped tail portion. As used herein, the term "ring electrode" is intended to include both circumferentially closed and circumferentially open conductive rings dimensioned to receive and be supported by and electrically connected to the electrode receiving pads on the exposed outer surface of the helically wrapped flat multiconductor tail portion. Also, as used herein, the term "overmolded" as applied to the ring electrodes is intended to encompass all known molding processes and procedures employed in the coating of cochlear electrodes with a suitable polymeric material, including, without limitation, the pre-coating masking of portions of such electrodes followed by a removal of the masking material to expose portions of the electrode, the coating of the electrodes using molding equipment including internal features that block the flow of the polymeric material to portions of the electrode leaving the electrode with exposed portions, and the post-coating use of polymeric material removal apparatus such as lasers to remove some of the coating to expose portions of the electrode.

Basically a process for manufacturing and processing the microcircuit integrated cochlear electrode array comprises the steps of securing and supporting a nonconductive film substrate, attaching a metallic ribbon to a surface of the substrate and machining a flat multiconductor microcircuit from the ribbon. The machined microcircuit includes (i) a flat elongated multiconductor tail portion with spaced outwardly exposed electrode receiving pads and (ii) a flat multiconductor head portion connected to the tail portion and having spaced vertically exposed circuit attachment pads. The flat microcircuit is laminated between the substrate and an insulating cover and the laminated microcircuit is then excised from the remaining film substrate with the electrode receiving pads exposed. The tail portion of the excised laminated microcircuit is then helically wrapped into a helix with the exposed electrode receiving pads extending around the insulating cover. Finally, ring electrodes are mounted on and electrically connected to the exposed electrode pads and the helically wrapped tail portion is overmolded with a suitable polymeric or plastic material readying the microcircuit for cochlear implant.

BRIEF DESCRIPTION OF ACCOMPANYING DRAWINGS

Figure 6:
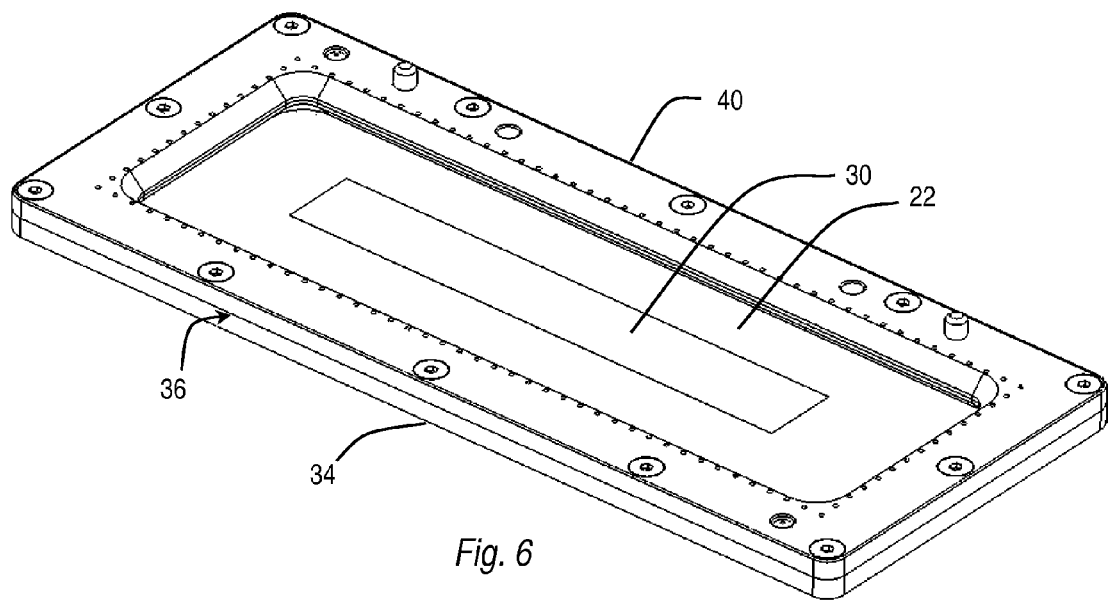
FIG. 6 shows the carrier and film substrate of FIG. 5 with a flat metallic ribbon attached to an upper surface of the film.
Figure 7:
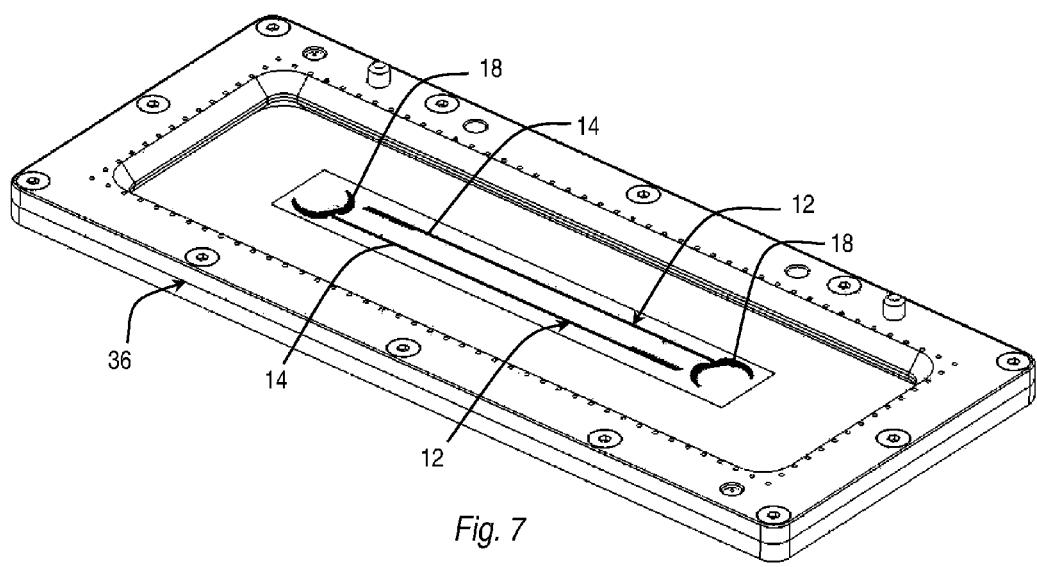
Figure 7A:
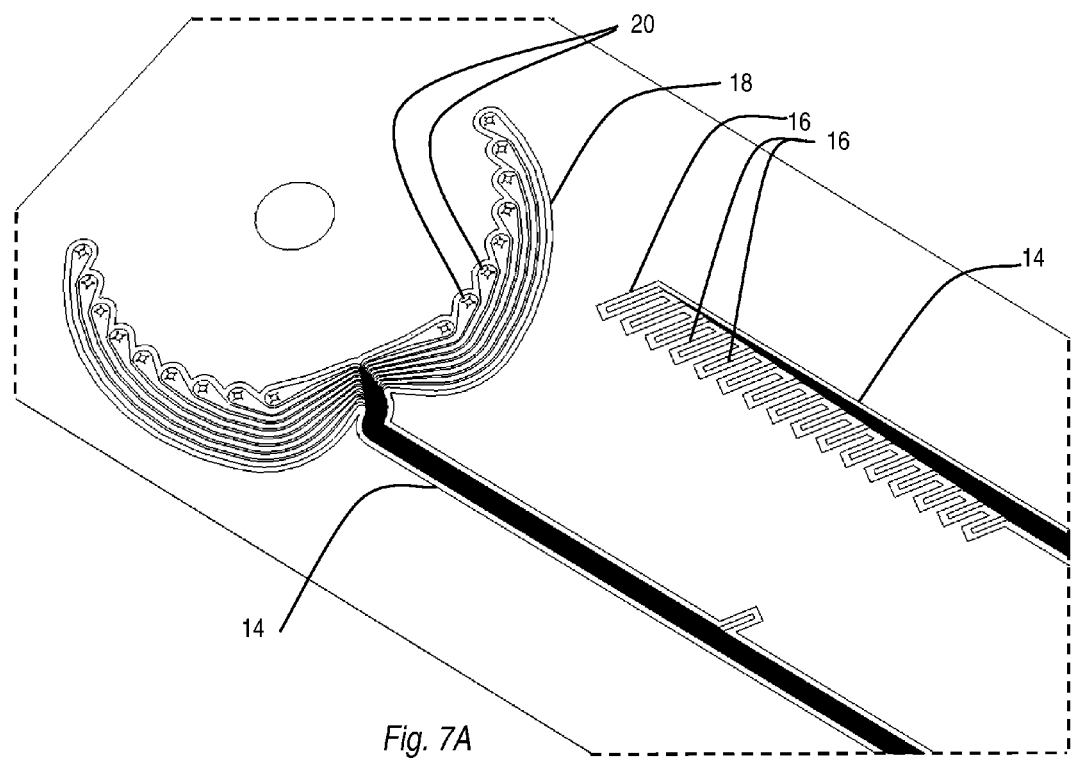
Figure 7B:
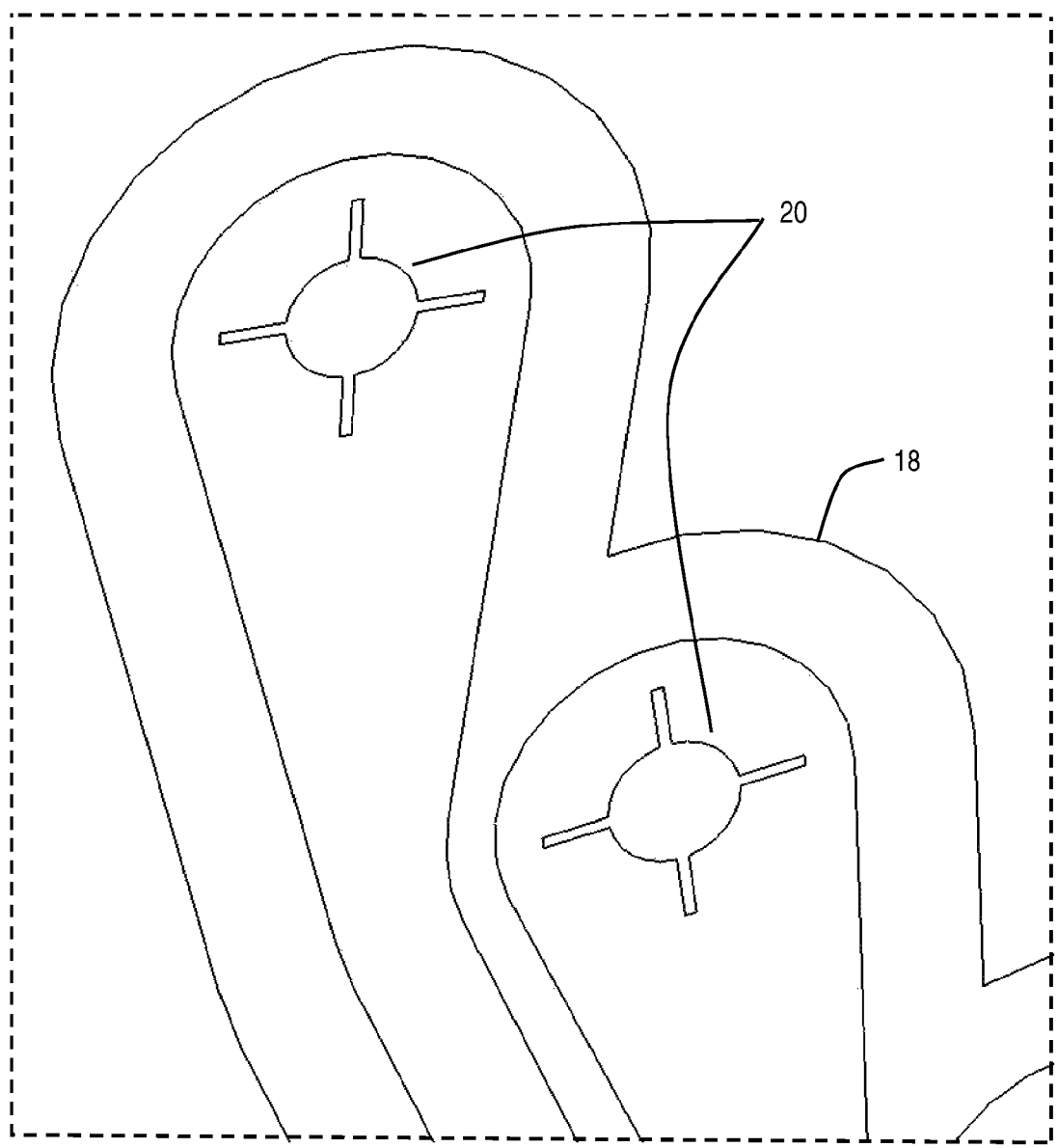
Figure 7C:
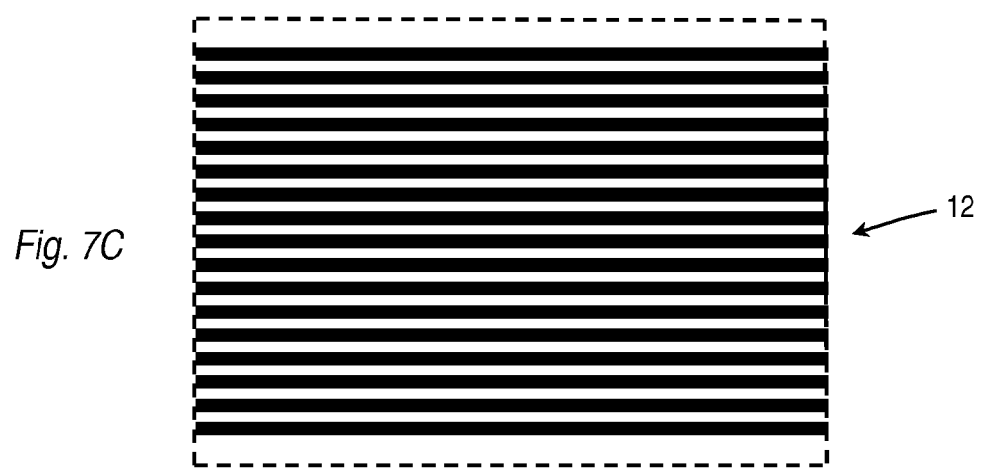

FIG. 7 shows two laterally spaced longitudinally extending multiconductor microcircuits machined by laser cutting the metallic ribbon attached to the upper surface of the film substrate shown in FIG. 6, each microcircuit including a flat elongated multiconductor tail portion with longitudinally spaced outwardly exposed ring electrode receiving pads and a flat multiconductor arc-shaped head portion with spaced circuit attachment or interconnect pads as shown more clearly in FIG. 7A and FIG. 7B respectively, FIG. 7C showing the close lateral spacing of laser cut individual conductors in the tail portion of the microcircuits.

Figure 8:
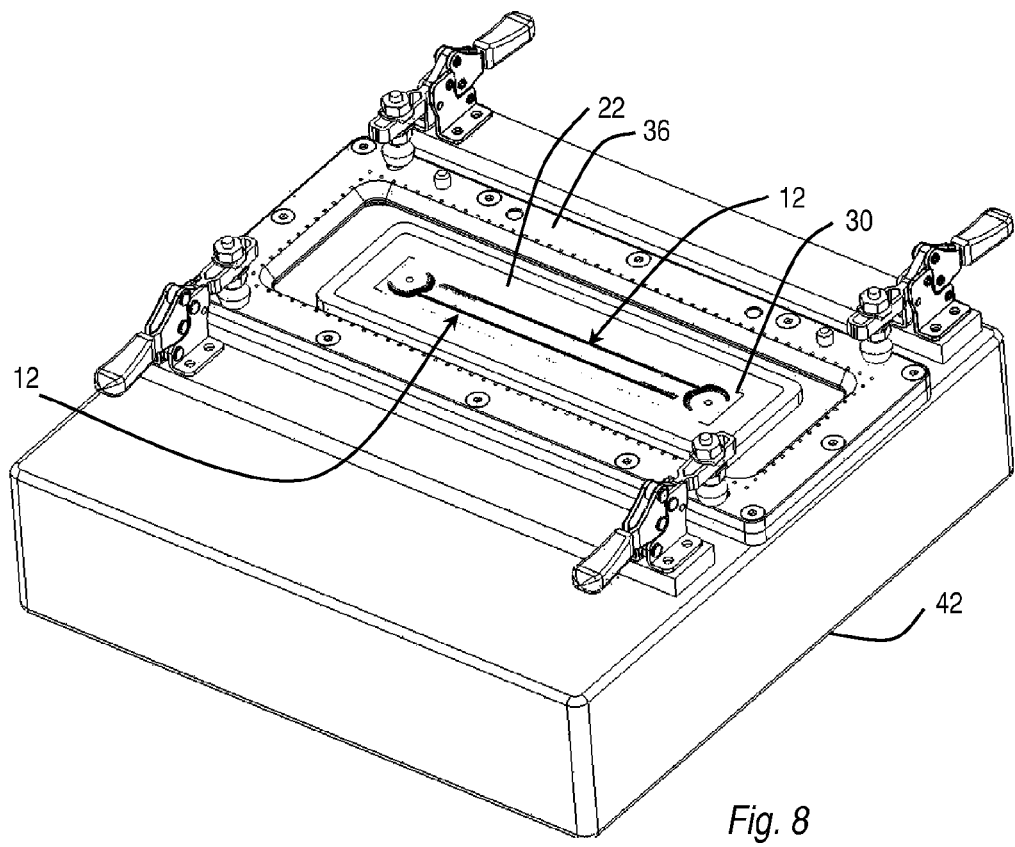

FIG. 8 shows the carrier and microcircuits of FIG. 7 clamped to a base of a heated ceramic vacuum chuck prior to overmolding with a silicone layer.

Figure 9:
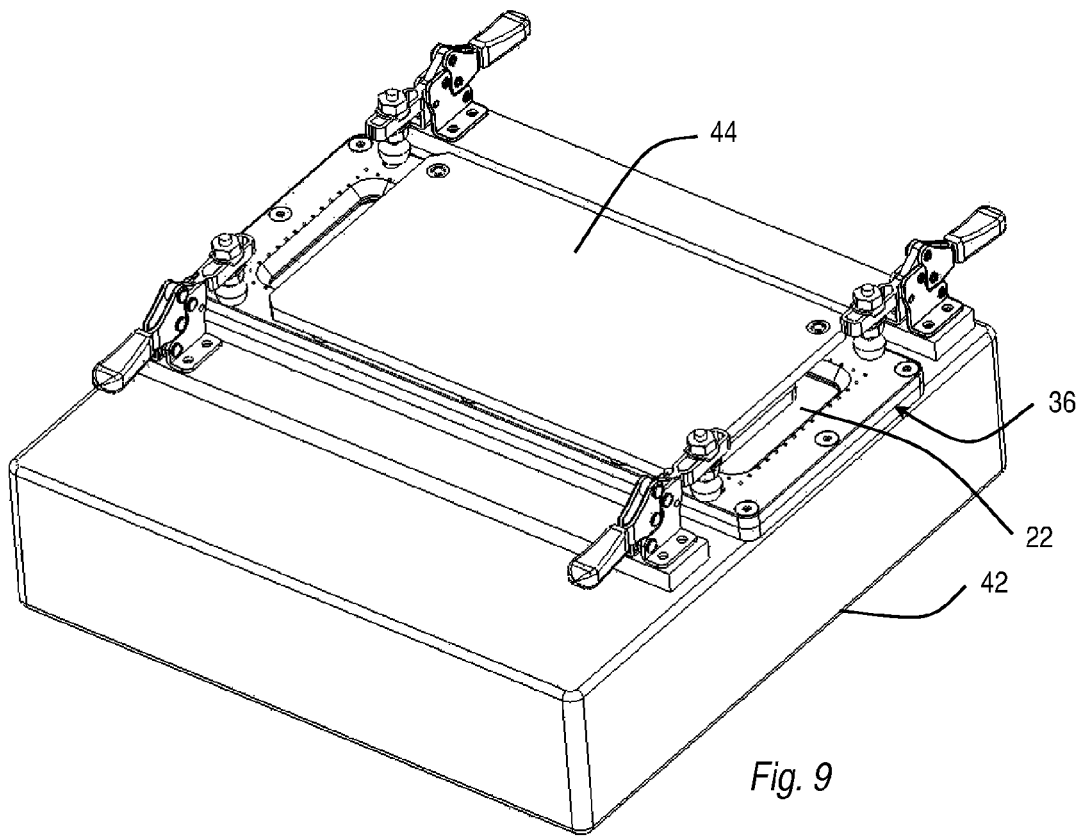

FIG. 9 shows the carrier and chuck of FIG. 8 with an overmold plate covering the carrier and including lower features that shut-off and create exposed areas on the ring electrode receiving pads and interconnect pads.

Figure 10:
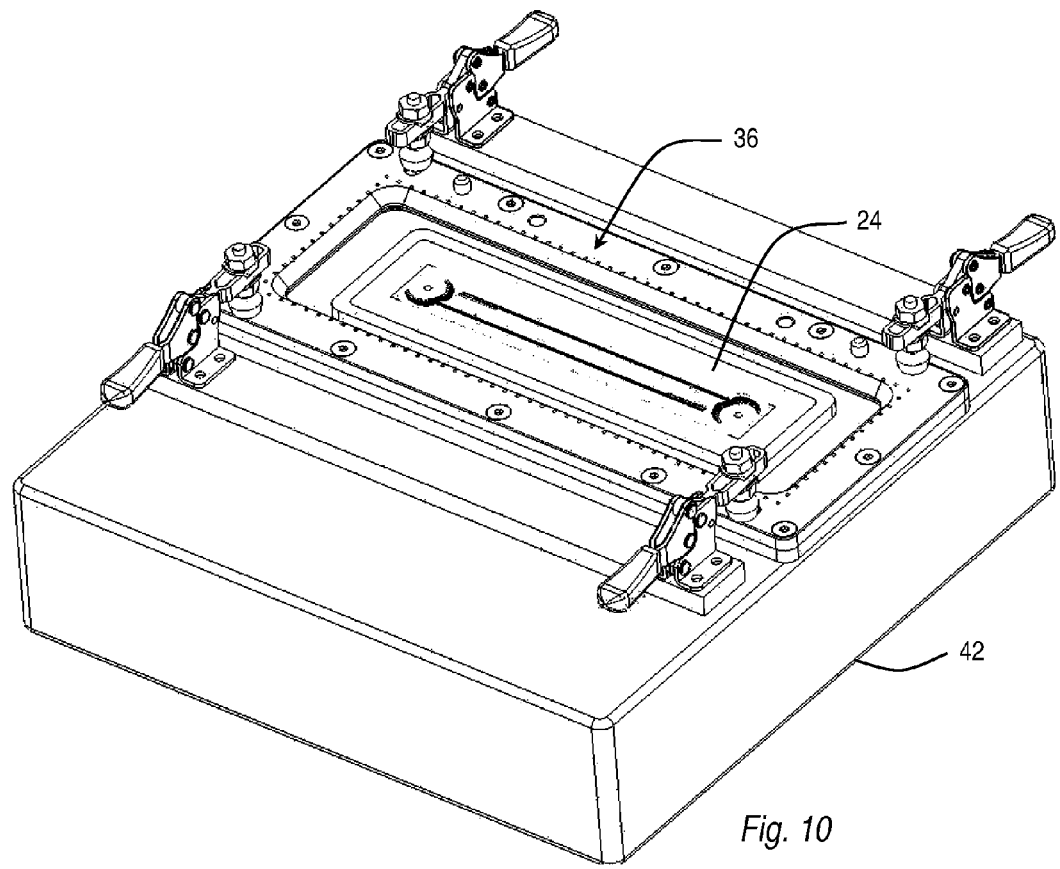

FIG. 10 shows the carrier and microcircuits of FIG. 8 after the overmolding step has been completed and the microcircuits are laminated between the silicone layer and the film substrate.

Figure 11:
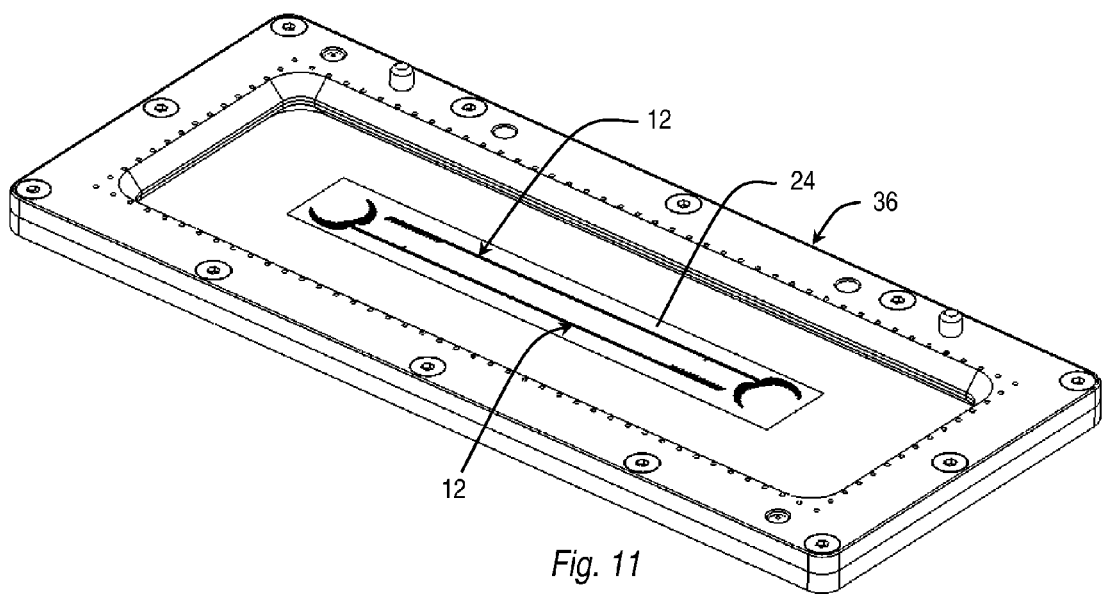

FIG. 11 shows the carrier and laminated microcircuits removed from the ceramic vacuum chuck of FIGS. 8-10.

Figure 12:
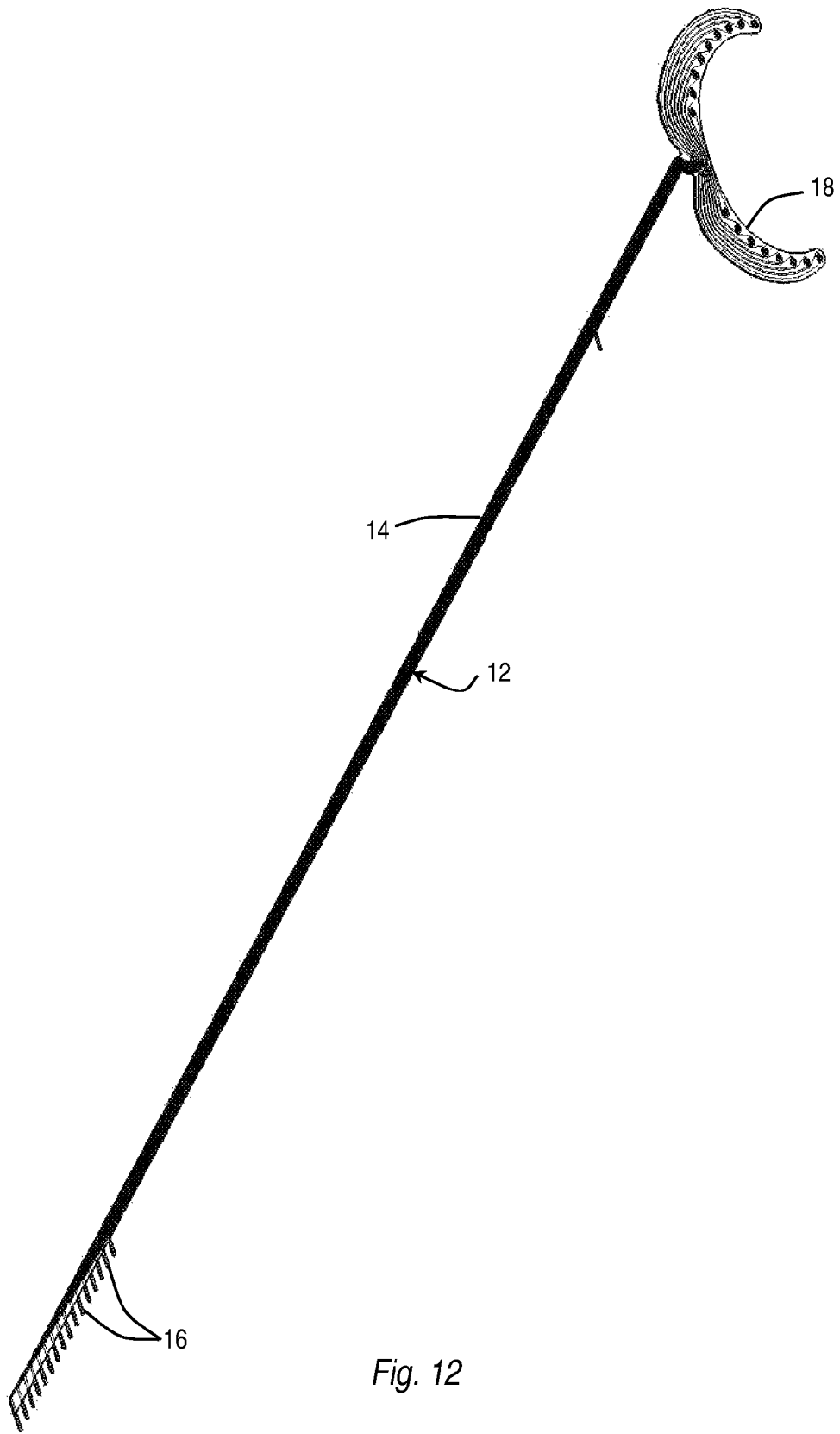

FIG. 12 shows the microcircuits completely excised from the carrier as by laser cutting through both the silicone and film substrate layers.

Figure 13A:
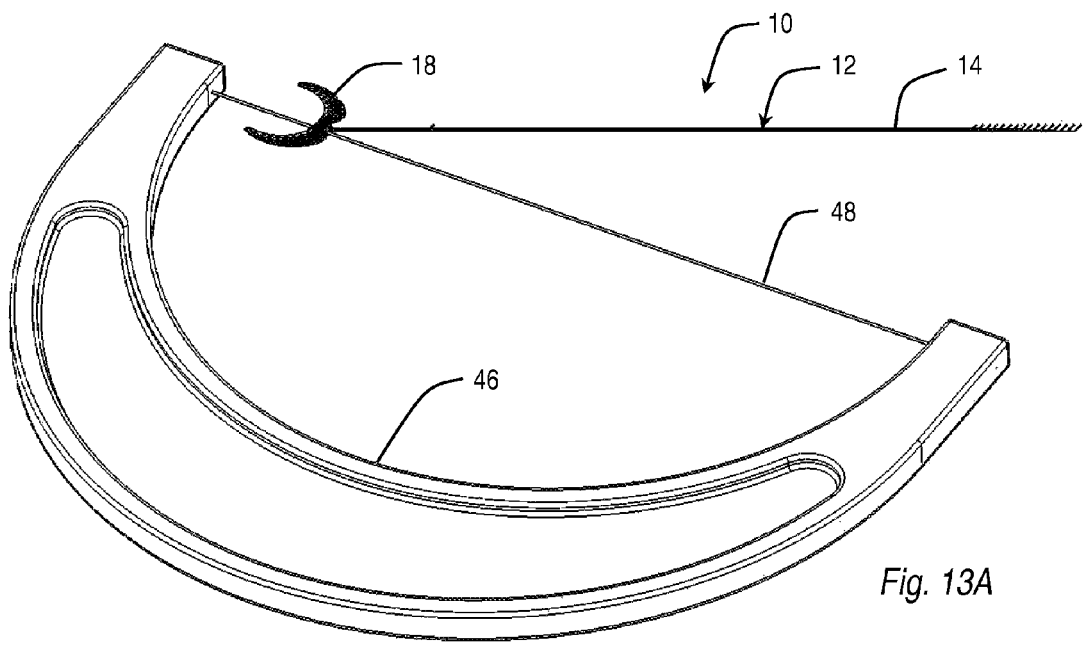

FIG. 13A shows the head portion of one of the microcircuits clamped to a tooling bow having a tensioned wire extending between ends of the bow and used first to receive a series of platinum electrode rings and then after tensioning by the bow to receive the tail of the microcircuit as it is wrapped into a helical shape and to suspend the microcircuit during subsequent overmolding processes.

Figure 13B:
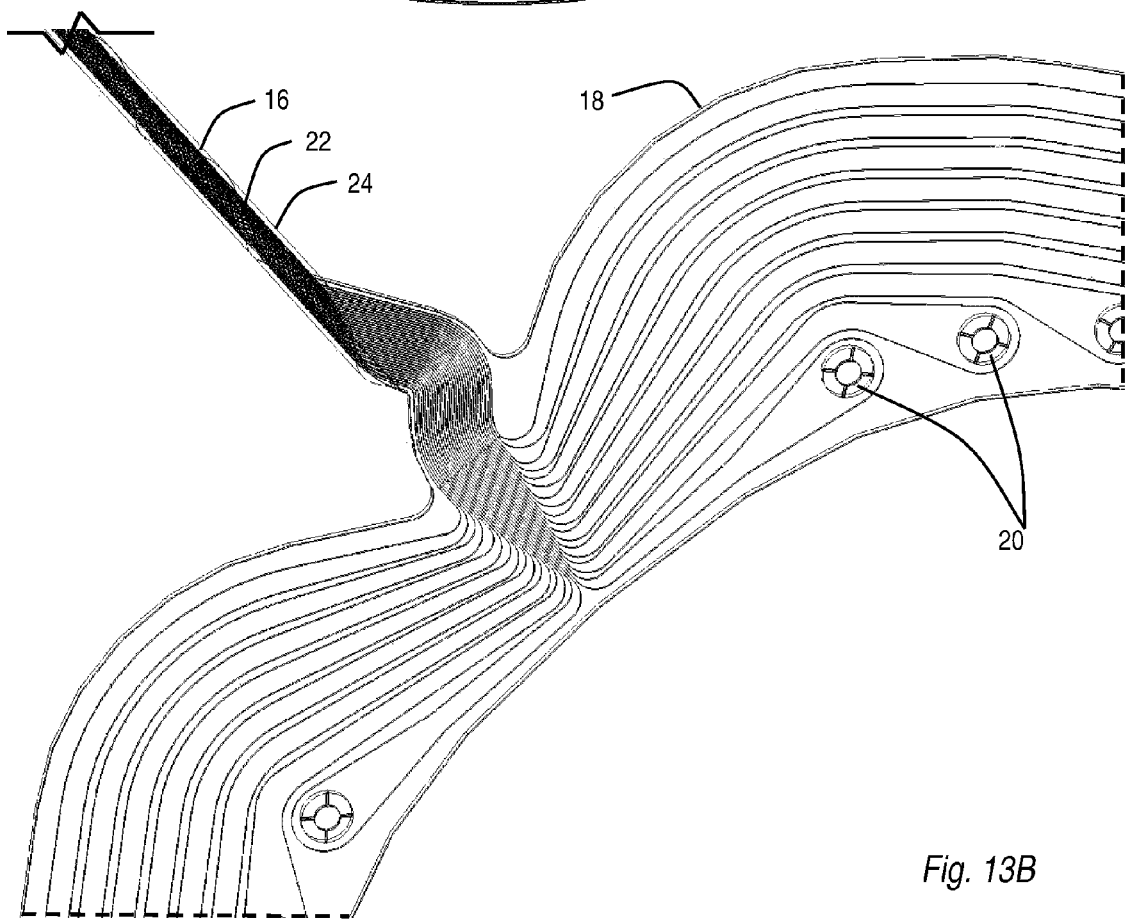

FIG. 13B shows the head portion of the microcircuit extending from the tensioned wire of the tooling bow and the tail portion wrapped in a helix around the tensioned wire with the ring electrode receiving pads exposed on an outer surface of the helix.

Figure 14A:
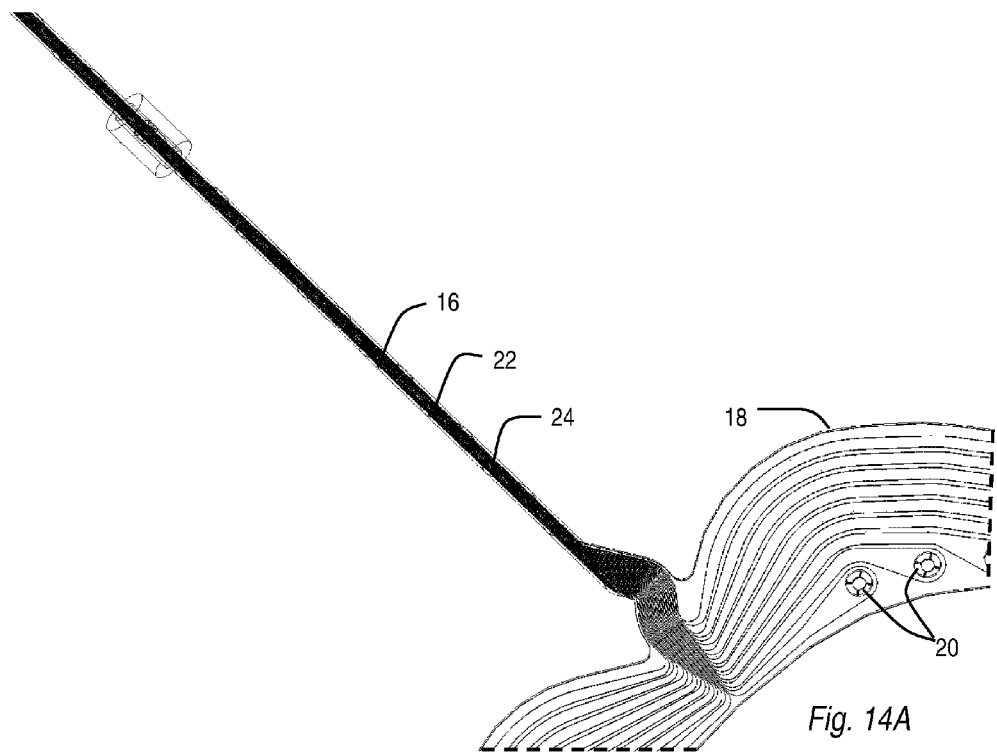

FIG. 14A shows the head and tail portions of the microcircuit as illustrated in FIG. 13B with a ring electrode being positioned over an exposed receiving pad of the microcircuit.

Figure 14B:
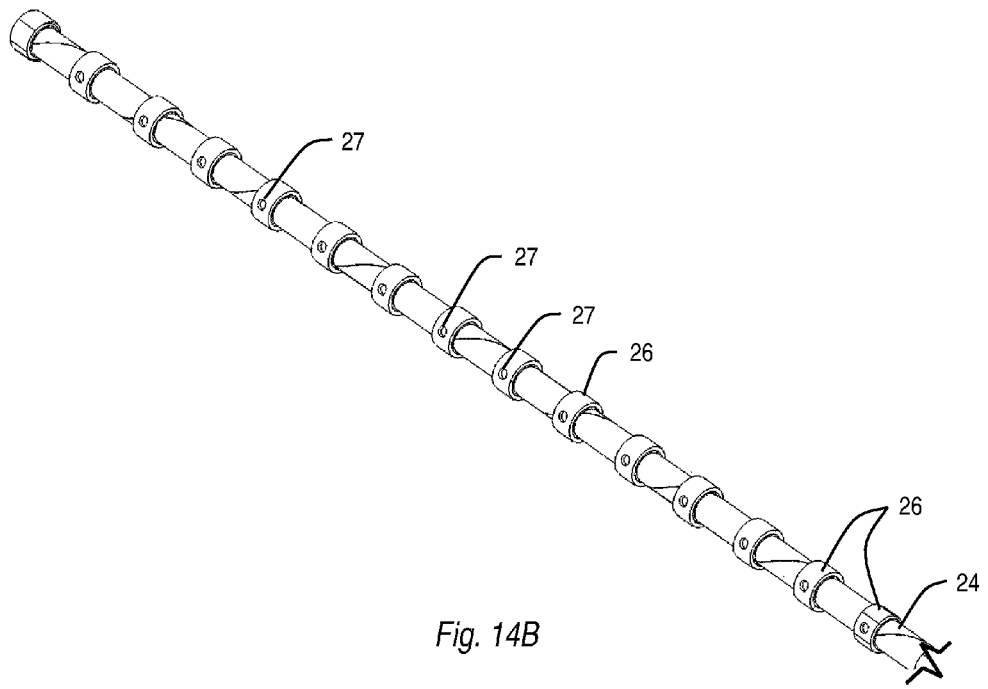

FIG. 14B shows a series of ring electrodes on the helically wrapped tail portion of the microcircuit each ring being positioned over a different electrode receiving pad with a hole in the ring electrode aligned with its supporting pad for future laser welding to the pad.

Figure 14C:
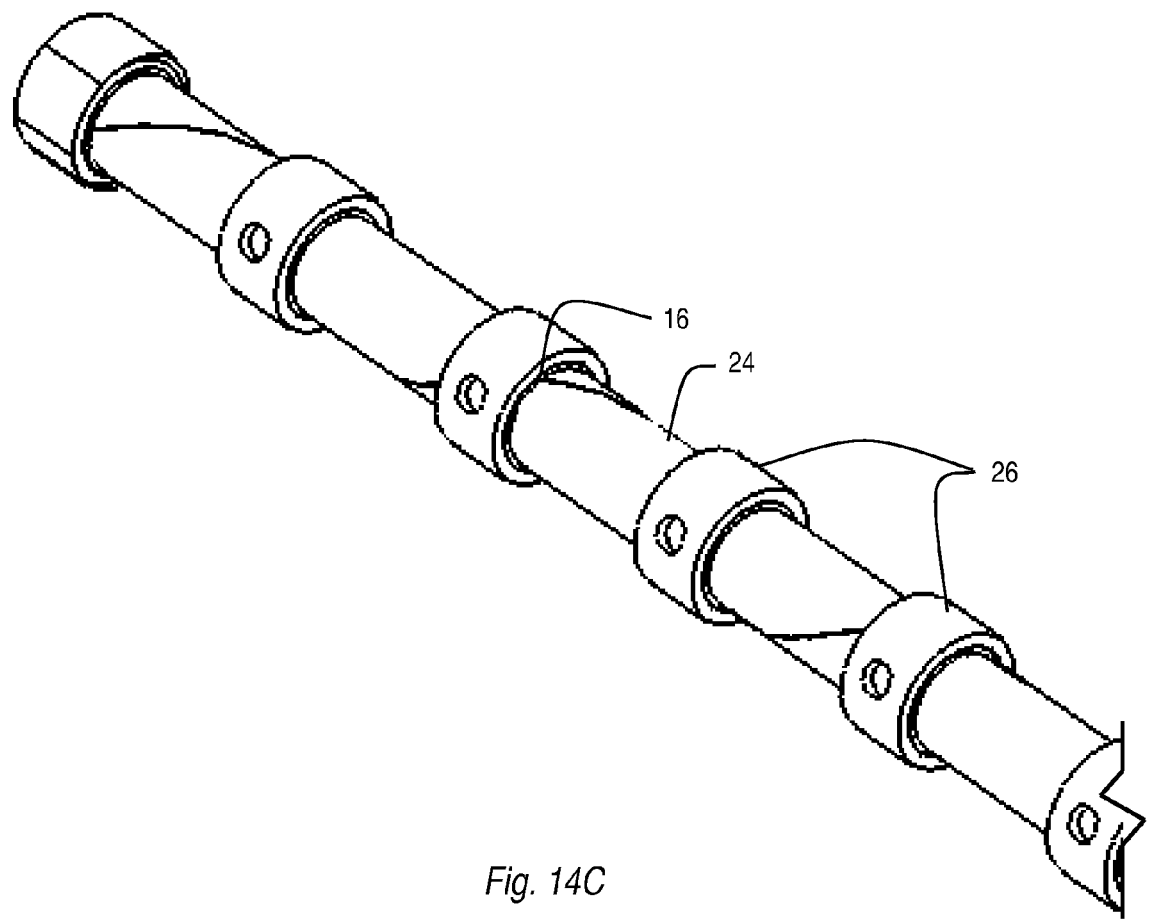

FIG. 14C in an enlarged showing of a portion of the helically wrapped portion of FIG. 14B depicting each electrode as laser welded to its supporting pad.

Figure 15:
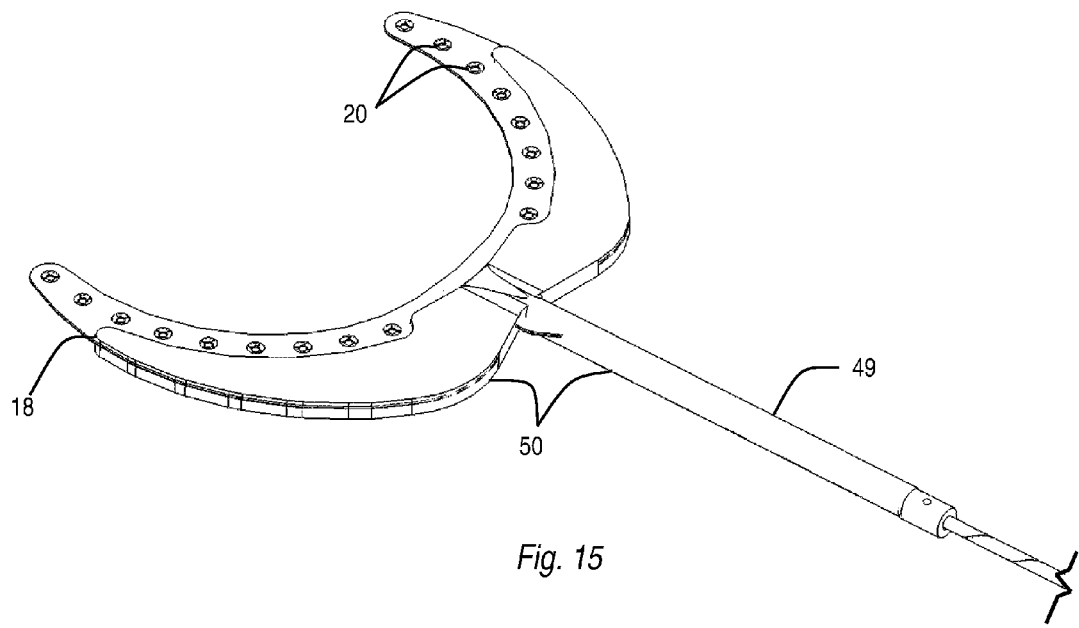

FIG. 15 shows the microcircuit supported on the tensioning wire of the tooling bow after a first overmold that encapsulates the wrapped electrode up to its first ring electrode and the underneath of the interconnect circuit of the head portion of the microcircuit creating a silicone stand-off for the head portion.

Figure 16:
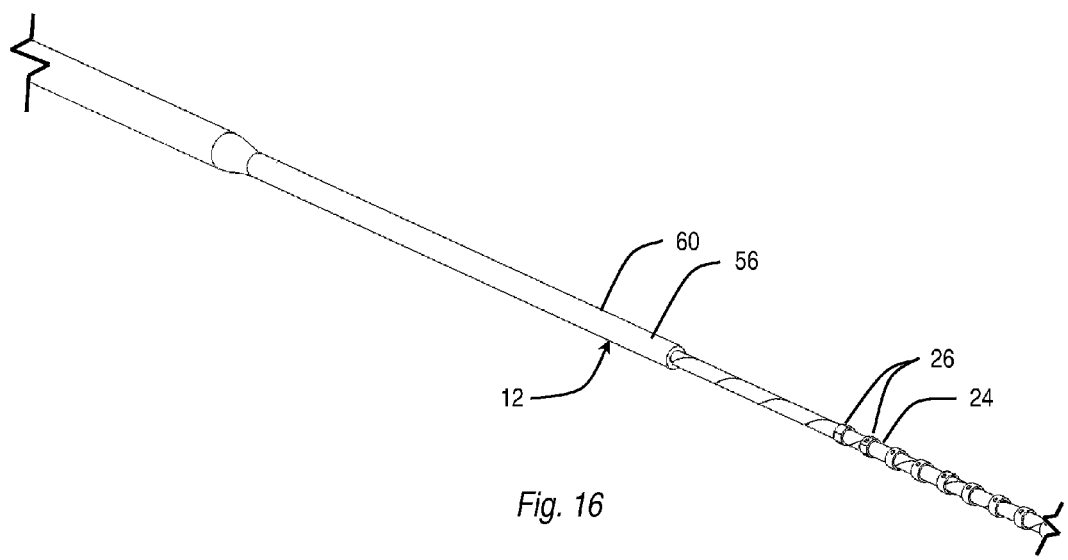

FIG. 16 shows the microcircuit supported on the tensioning wire of the tooling bow after a second overmold that encapsulates the wrapped electrode out to the end of the electrode subassembly with the overmold decreasing in diameter as it approaches the first visible ring electrode.

Figure 17A:
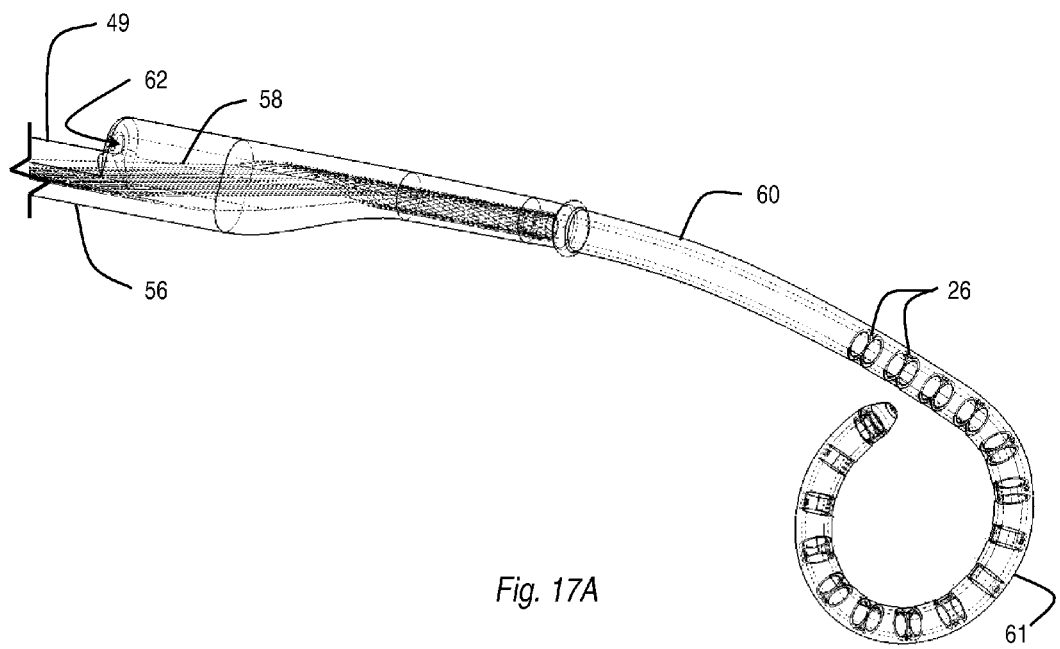

FIG. 17A shows the overmolded electrode subassembly of FIG. 16 after completion of a third overmolding process that was preceded by the subassembly having been removed from the tooling bow and an end of the microcircuit unwrapped offsetting the electrode and creating a stylet lumen into which a stylet was placed and the electrode and stylet placed into overmold tooling for overmolding.

Figure 17B:
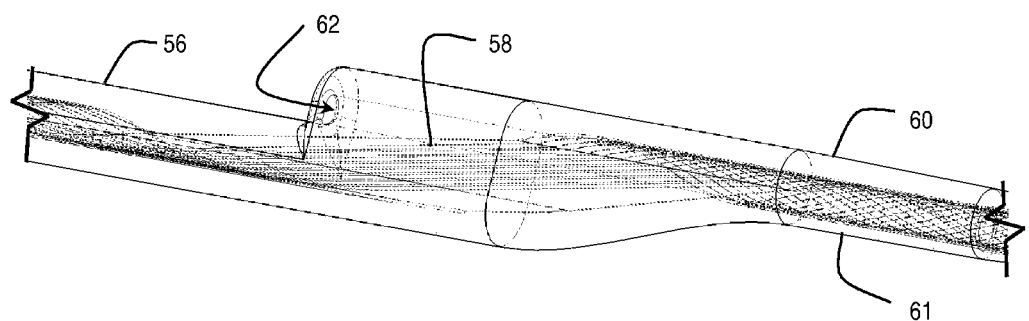

FIG. 17B is an enlarged showing of a portion of the electrode assembly of FIG. 17A including the unwrapped microcircuit and stylet lumen.

Figure 18A:
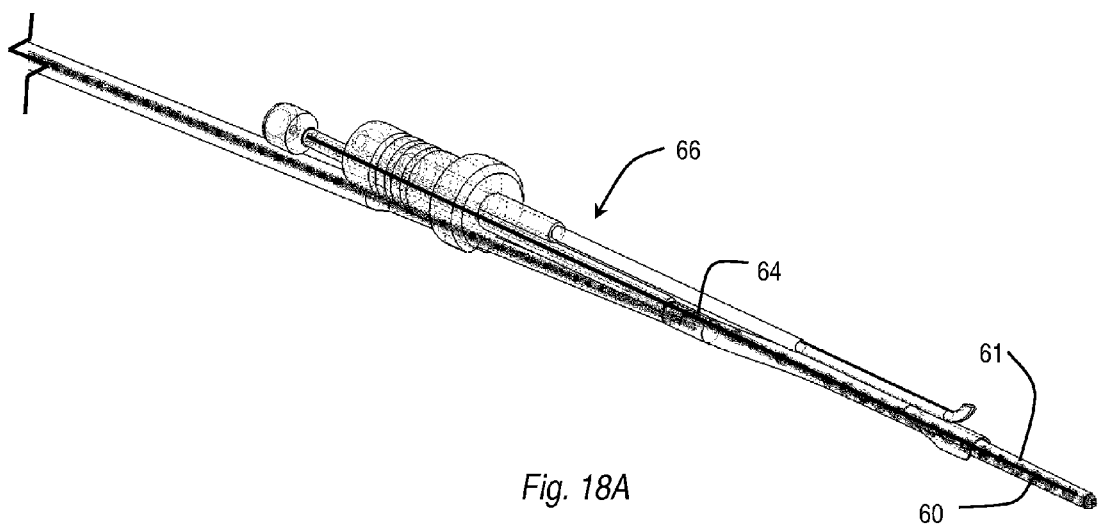

FIG. 18A a conventional stylet insertion tool inserted into the lumen of the electrode subassembly straightening the electrode for insertion.

Figure 18B:
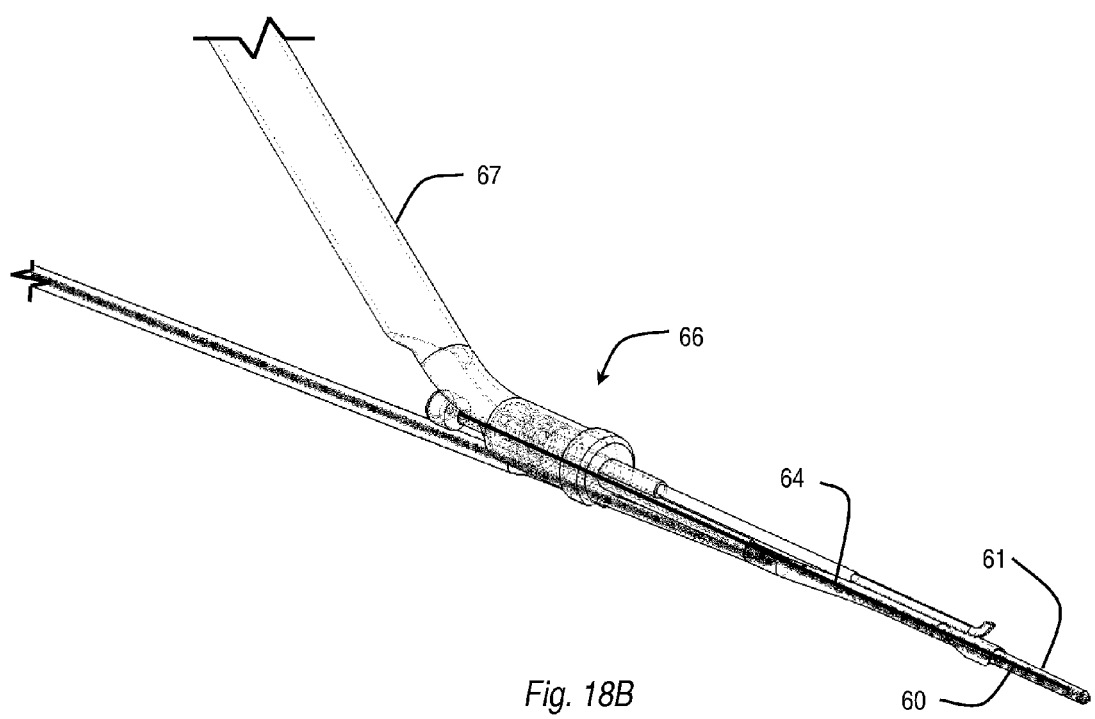

FIG. 18B shows the stylet insertion tool rotated 90 degrees to show the handle of the tool.

Figure 19:
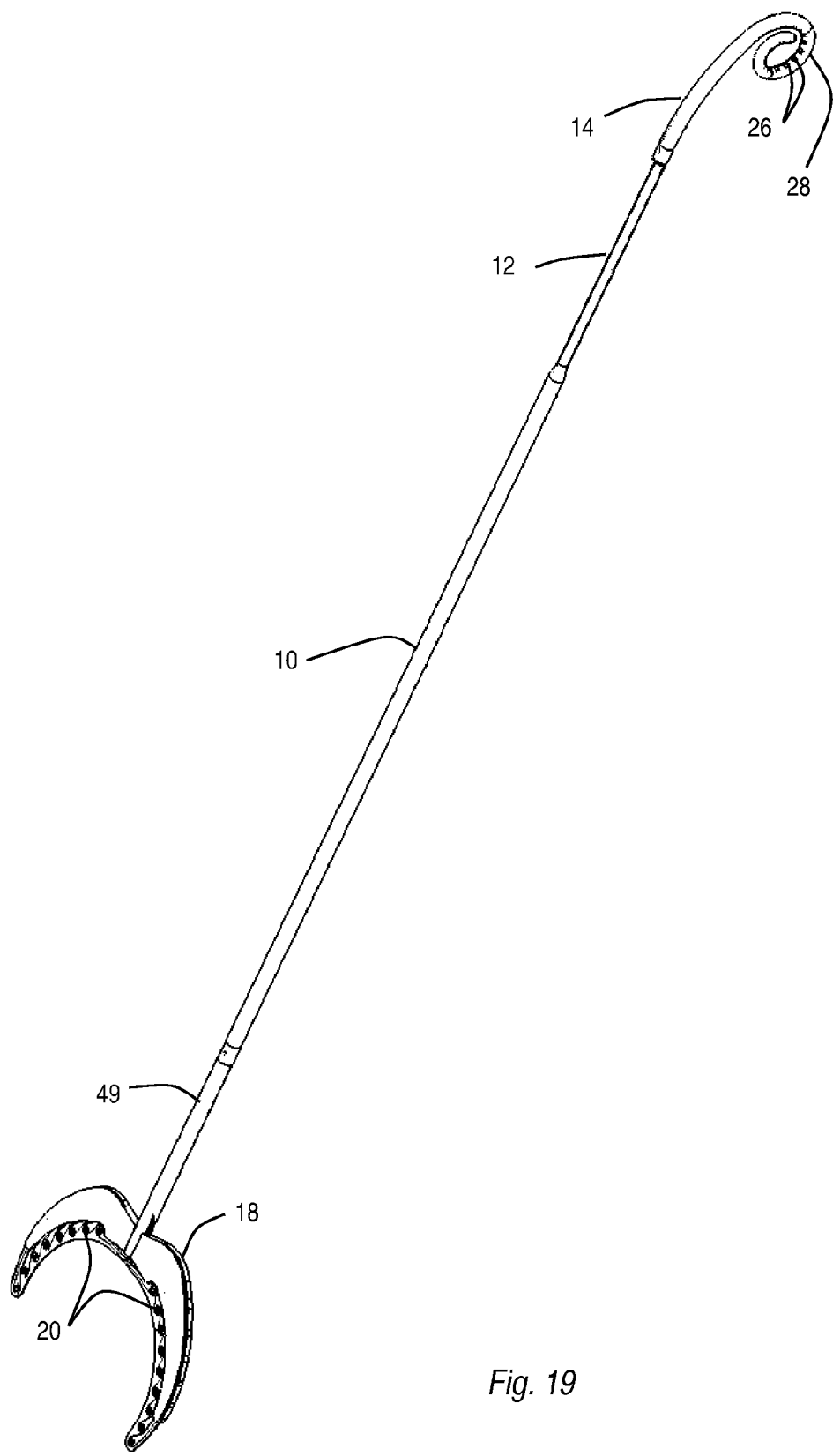
Figure 20A:
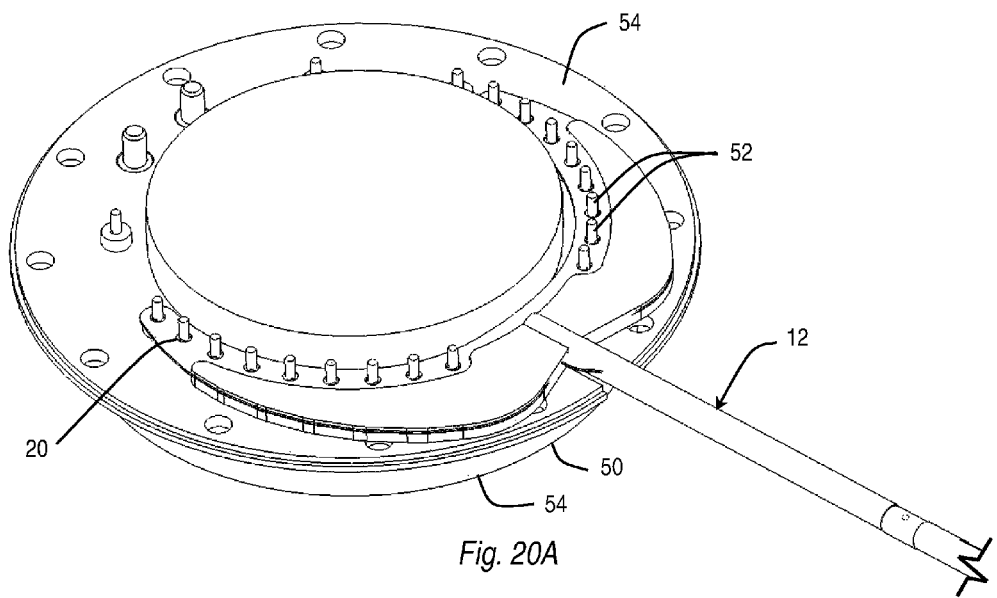
Figure 20B:
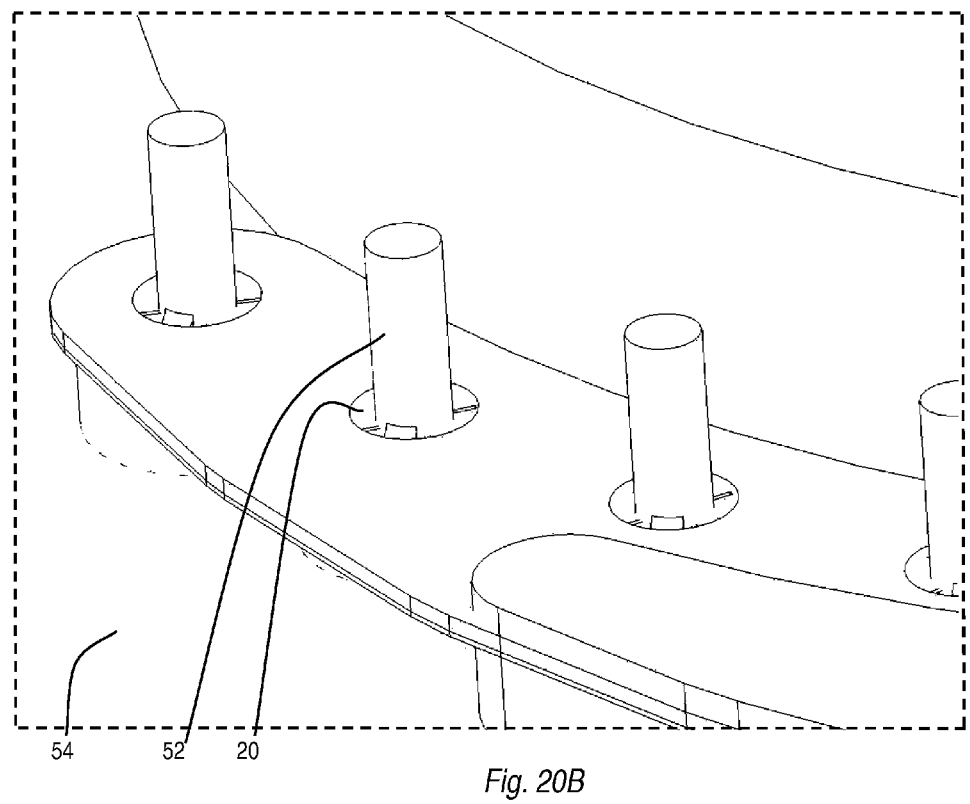

FIG. 19 shows the completed helix electrode assembly ready for attachment of its head portion to the platinum feedthrough posts of a titanium housing as shown in FIGS. 20A and 20B.

FIGS. 20A and 20B show a titanium housing where the microcircuit interconnect pads slit slightly during laser machining make intimate contact with corresponding ones of the feedthrough posts for laser welding to the posts.

DETAILED DESCRIPTION OF INVENTION

As shown in FIG. 19, the process of the present invention is intended to efficiently produce a new and improved microcircuit integrated cochlear electrode array 10, that comprises multiconductor microcircuit 12 including a multiconductor tail portion 14 with longitudinally spaced outwardly exposed electrode receiving pads 16 (see FIGS. 7A and 12) and a flat multiconductor head portion 18 connected to the tail portion and having spaced outwardly exposed circuit attachment pads 20 (see FIGS. 13B, 15, 19, 20A and 20B). The tail and head portions 14 and 18 are laminated between a nonconductive film substrate 22 (see FIGS. 3-5) and an insulating cover 24 (see FIG. 10). As shown in FIGS. 14C and 17B, the tail portion 14 is helically wrapped into a helix with the electrode receiving circuit attachment pads 16 exposed to and carrying ring electrodes 26 overmolded with a plastic material 28 (see FIG. 17A). As also shown in FIGS. 17A and 17B, a portion of the tail portion 14 may be unwrapped at a junction 58 with a section 60 including the ring electrodes 62 offsetting an electrode section 49 and creating a lumen 62 for receiving a stylet 64 as shown in FIGS. 18A and 18B.

Figure 1A:
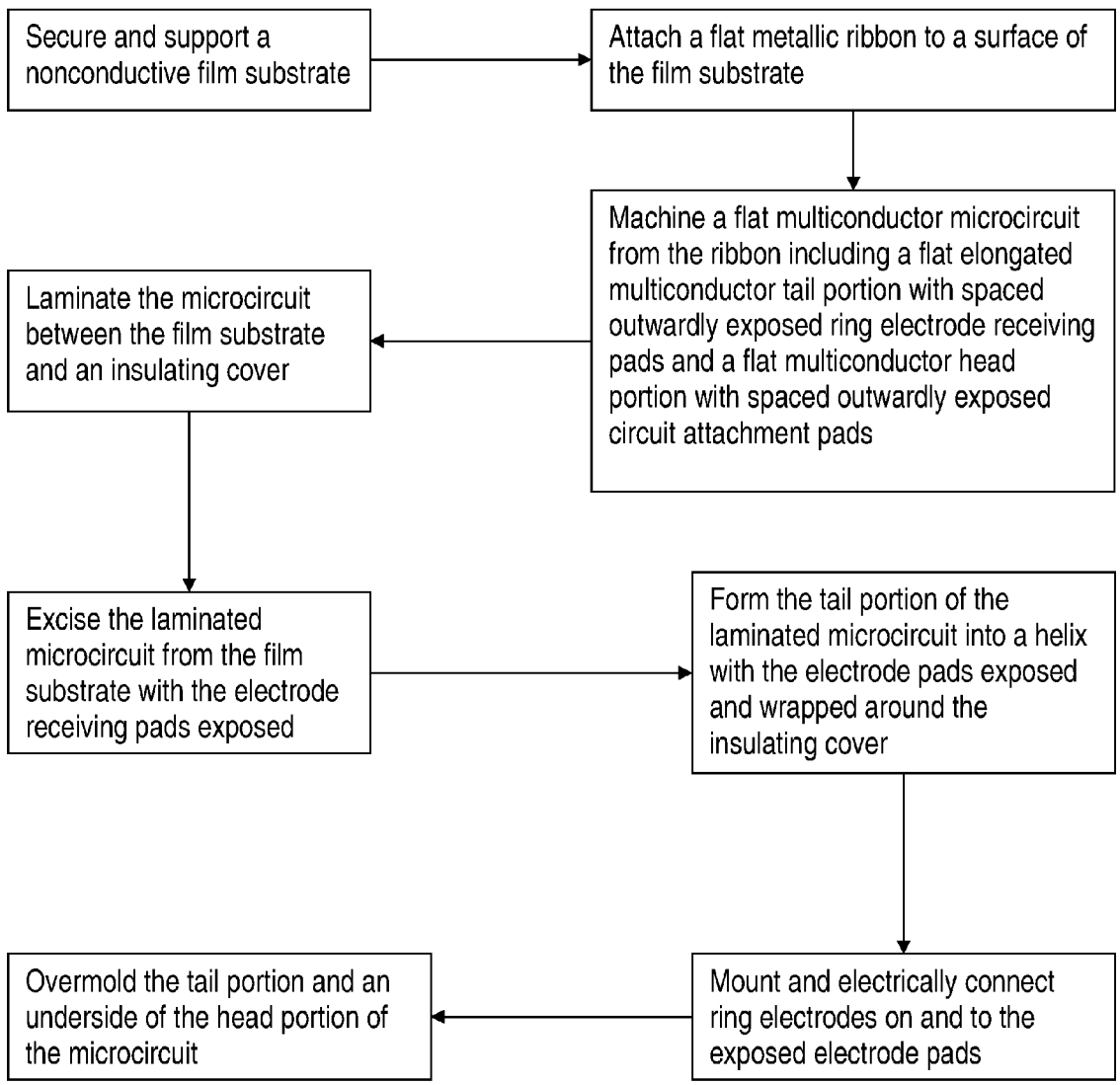
FIG. 1A is a flow chart of the basic steps central to the manufacturing process of the present invention.
Figure 1B:
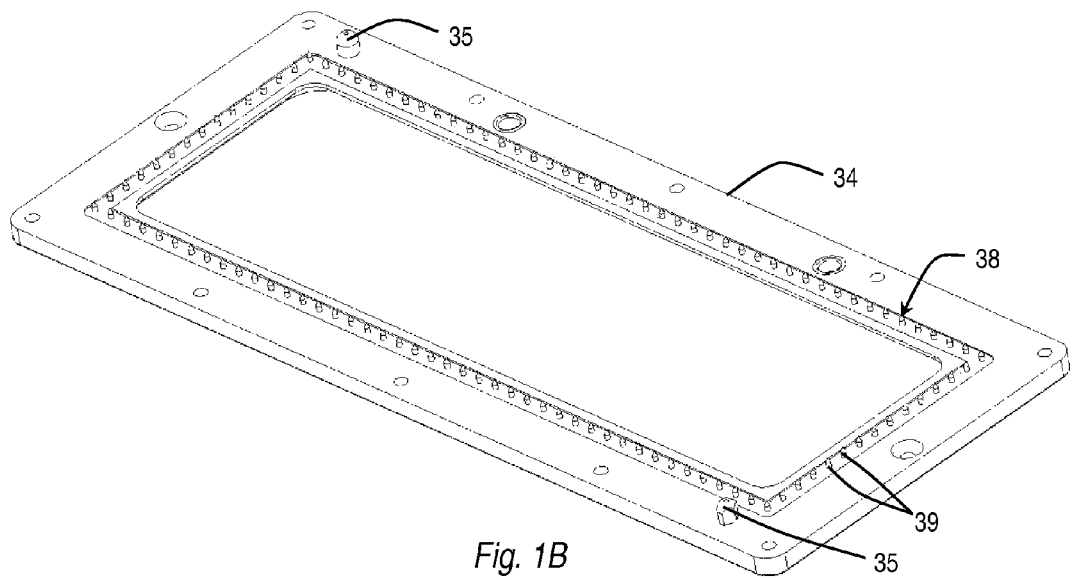
FIG. 1B shows a basic form of a lower frame of a carrier utilized in the process steps of securing and supporting a nonconductive film substrate.

To produce such an electrode array, the process of the present invention basically comprises the steps of the flow diagram of FIG. 1A. As represented in FIG. 1A, and as illustrated in accompanying FIGS. 1B-20B, the process comprises securing and supporting the nonconductive film substrate 22; attaching a metallic ribbon 30 to a surface of the substrate 22; machining at least one flat multiconductor microcircuit 12 from the ribbon 30 including the flat elongated multiconductor tail portion 14 with longitudinally spaced outwardly exposed ring electrode receiving pads 16 and the flat multiconductor head portion 18 connected to the tail portion and having spaced outwardly exposed attachment pads 20; laminating the flat microcircuit 12 between the film substrate 22 and the insulating cover 24; excising the laminated microcircuit 12 from the film substrate 22 with the electrode receiving pads 20 exposed; helically wrapping the tail portion 14 of the excised laminated microcircuit 12 into a helix with the exposed electrode receiving pads 16 wrapped around the insulating cover 24; mounting and electrically connecting the ring electrodes 26 on and to the exposed electrode pads 16; and overmolding the helically wrapped tail portion 14 with the plastic material 28 to ready the microcircuit for cochlear implant.

With regard to the securing of the nonconductive film substrate 22 and a shown in FIGS. 1B-5, a roll 32 of the nonconductive film substrate 22, such as a roll of nonconductive plastic, is positioned adjacent an end of a lower open frame 34 of a carrier 36 utilized in the process steps of securing and supporting the nonconductive film substrate.

Figure 2:
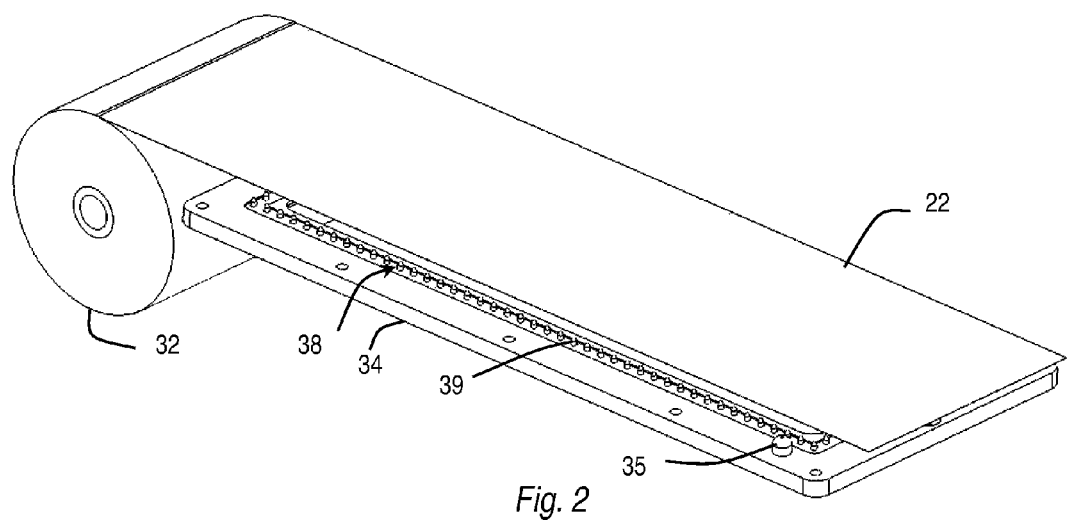
FIG. 2 shows a length of the nonconductive film substrate extending from a roll over the lower frame of FIG. 1B.

As represented in FIG. 2, a length of the film substrate 22 is drawn from the roll 32 to extend over the top of the open frame 34. Preferably, the film substrate 22 is maintained under tension in both X and Y directions while positioned over the open frame.

Figure 3:
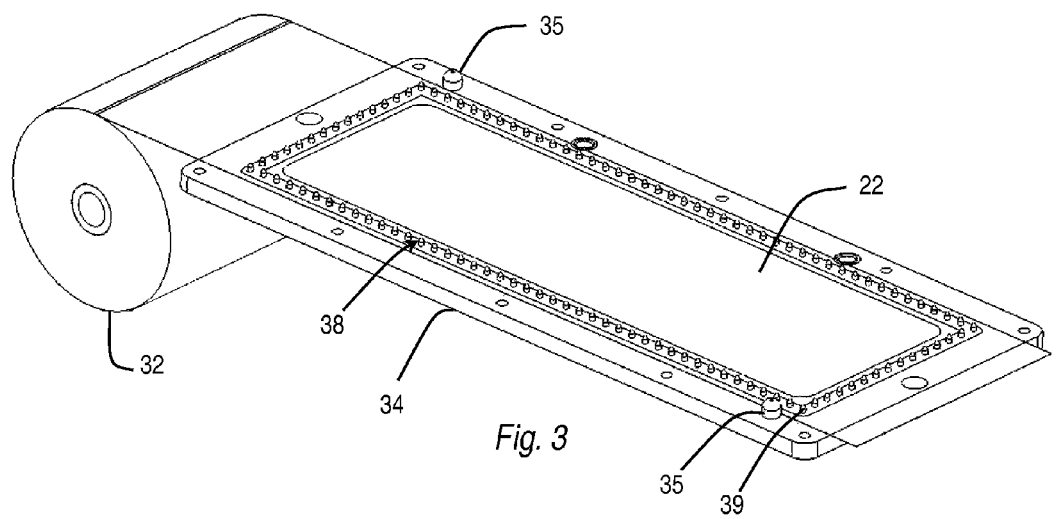
FIG. 3 shows the length of film substrate after it has been lowered onto the lower frame and releasably secured thereto by attachment means extending vertically from the lower frame.

As represented in FIG. 3, the length of film substrate 22 is then moved downward relative to the lower open frame 34 until attachment means 38, such as upwardly projecting pins 39, engage and penetrate a lower surface of the film substrate securing the tensioned length of film substrate 22 to the lower open frame.

Figure 4:
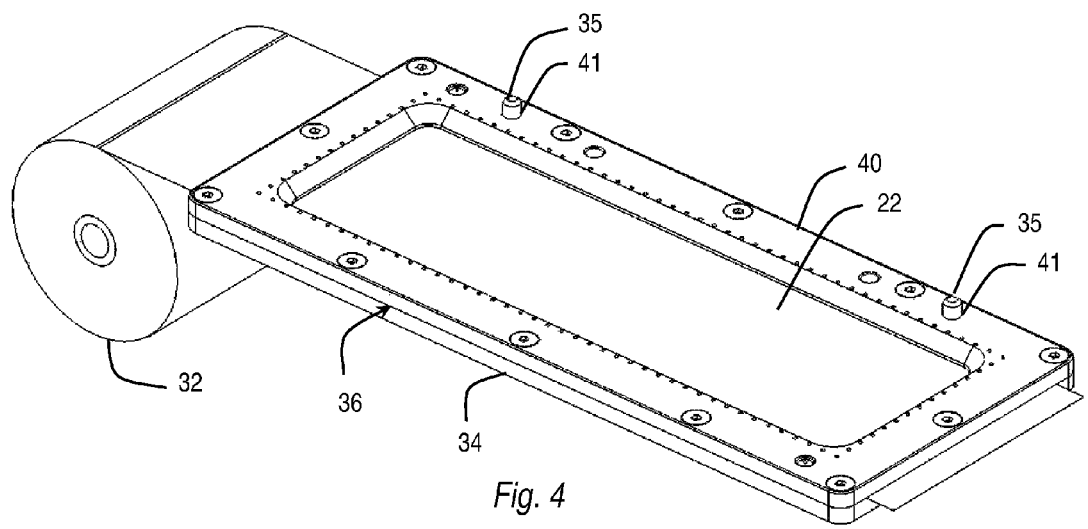
FIG. 4 shows the length of film substrate clamped and secured between the lower frame and an upper frame of the carrier.
Figure 5:
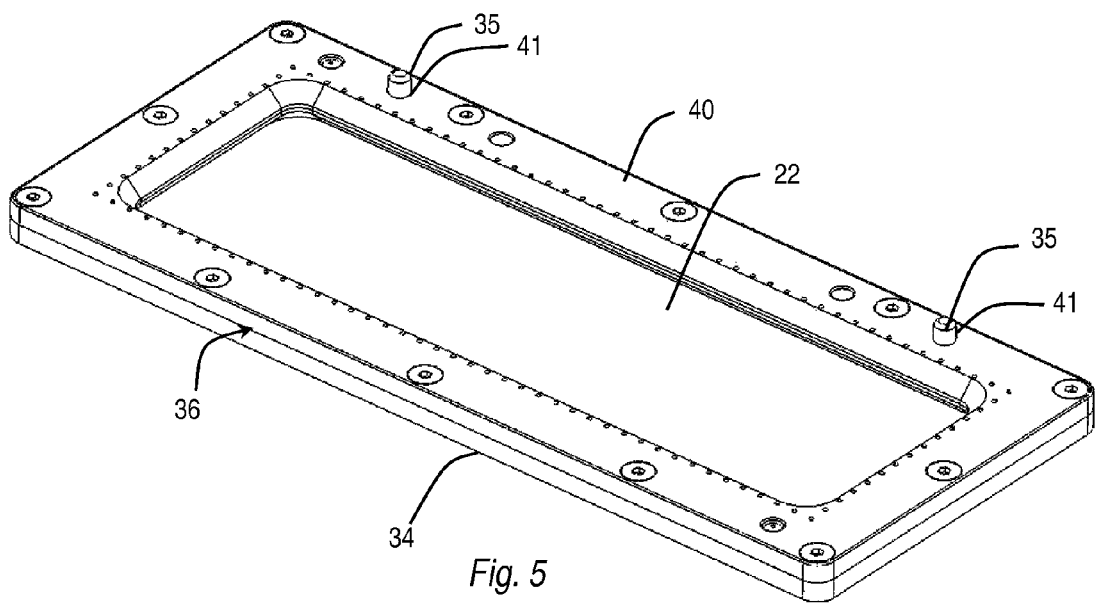
FIG. 5 shows the length of film substrate secured by the carrier after all excess film has been trimmed from the carrier and the roll of film has been removed.

As represented in FIG. 4, an upper open frame 40 of the carrier 36 is then positioned over and on the lower open frame 34 with alignment holes 41 in the upper frame receiving alignment pins 35 extending upward from the lower frame 34 and the upper frame secured to the lower frame as by screws clamping the length of tensioned film substrate within the carrier 36. Excess film is then trimmed from the carrier 36 and separated from the roll 32 of plastic as depicted in FIG. 5.

As indicated in FIG. 1A, after the film substrate has been secured and supported, the next step in the process of the present invention is the attachment of the flat metallic ribbon 30 to a surface of the film substrate 22 shown in FIG. 6. In practice this is accomplished by placing the carrier 36 and the metallic ribbon 30, preferably a platinum iridium ribbon, into a standard plasma etching machine (not shown) where mating surfaces of the film substrate 22 and the ribbon 30 are etched. The carrier 36 and the etched platinum ribbon 30 are then placed into a standard thermal heating fixture (not shown) with tooling liners located on the carrier. In this regard, the platinum ribbon 30 is carefully placed into a transfer fixture (not shown) so that the ribbon is aligned relative to the tooling liners located on the carrier 36. Upon activation of the of the transfer fixture, the ribbon 30 is lowered onto the etched surface of the film substrate 22 where pressure and heat are applied for a prescribed time period to secure the ribbon to the film substrate.

Once the platinum ribbon 30 is secured to the film substrate 22, one or more flat multiconductor microcircuits 12 of the previously described structure are machined from the ribbon as depicted in FIGS. 7, 7A and 7B; FIG. 7C depicting the spacing of the parallel laser machined conductors of the two microcircuits 12 as being approximately 25 micron in width with 25 micron kerfs between the conductors. Preferably, the machining is achieved using laser machining with a femtosecond impulse laser machining center such as the commercially available Clark-MXR Femtosecond Impulse Laser Machining Center.

By way of comparison, traditional lasers first melt the material being machined and then vaporize it. Femtosecond laser light pulses are about one quadrillionth of a second in time duration and bypass the material melt phase and transition directly into the vapor phase thus creating very little heat and no slag or damage to surrounding areas. Also, femtosecond light pulses are capable of creating sub-micron features down to 50 nm and are wavelength independent and capable of machining any material.

After the microcircuits 12 are laser machined in the ribbon 30, the upper surface of the platinum ribbon is plasma etched and the carrier 36 is placed on a conventional heated ceramic vacuum chuck 42 and clamped in place as shown in FIG. 8 for conventional overmolding and lamination of the microcircuits between the film substrate 22 and the previously referenced insulating cover 24. In these regards, and as represented in FIG. 9, an overmolding mold plate 44 is installed over the exposed microcircuits 12 using tooling pins (not shown) located on a top cover of the carrier 36. The mold plate 44 is designed with shut-off features that will expose the ring electrode receiving pads 16 and the interconnect pads 20 during the subsequent operation of the heated vacuum chuck 42 and lamination of the microcircuits between the film substrate 22 and the insulating cover 24. Accordingly, when the heated ceramic vacuum chuck 42 and the enclosed carrier 36 reach a prescribed temperature, de-gassed silicone is injected between the carrier 36 and the mold plate 44 and a thin film of silicone comprising the insulating cover 24 is created around and between the features of the microcircuits 12 while the ring electrode receiving pads 16 of the tail portion 14 and the interconnect pads 20 of the head portion 18 remain exposed as depicted in FIGS. 10 and 11. FIG. 10 shows the assembly of FIG. 9 with the mold plate 44 removed. As an alternative to the overmolding steps shown in FIGS. 8-10, insulating cover 24 may be provided by laminating a second layer of film onto the microcircuits 12, adhering the second film layer to the microcircuits and to the exposed portions of film substrate 22.

After the above-described overmolding process is complete, the carrier 36 is placed in a femtosecond laser excising machine (not shown) and using the vision system built into the laser, the microcircuits are accurately aligned within the laser. The laser is then activated to cut completely through the silicone and nonconductive film layers comprising the insulating cover 24 and the film substrate 22 completely freeing the microcircuits 12 from the carrier 36 as depicted in FIG. 12.

Further processing operations of the process of the present invention preferably utilize a tooling bow 46 and a tensioned arbor wire 48 extending between opposite free ends of the bow as depicted in FIG. 13A. Basically, the tensioned arbor wire is used to wrap the tail portion 14 of one of the newly created microcircuits 12 into a helical shape and also suspend the electrode assembly 10 through various overmolding processes as will be described below.

In these regards, before installing the arbor wire 48 into the tooling bow 46 a series of the platinum electrode rings 26 are threaded onto the wire 48 prior to its tensioning on the bow. As depicted in FIG. 13A, the head portion 18 of one of the microcircuits 12 is then threaded onto the arbor wire 48 and clamped in place leaving the tail portion 14 of the microcircuit 12 free to be manually wrapped on the arbor wire 48. This is accomplished by placing the tooling bow 46 into a wrapping fixture along with the excised microcircuit 12. The tail portion 14 is then manually rotated around the arbor wire 48 such that edges of the silicone cover (or second film layer) 24 and film substrate 22 contact each other and the tail portion 14 forms a helix on the arbor wire 48 as shown in FIG. 13B. In this regard, FIG. 13B shows the head portion of the microcircuit extending from the tensioned wire of the tooling bow and the tail portion wrapped in a helix around the tensioned wire with the ring electrode receiving pads exposed on an outer surface of the helix.

It is important that while the tail portion 14 is wrapped on the arbor wire 48, the exposed ring electrode receiving pads 16 are wrapped around the silicone cover 24 in proper location or pitch along the tail portion of the microcircuit 12. After wrapping, the platinum electrode rings 26 pre-mounted on the arbor wire 48 are positioned by an operator one at a time on the wrapped and exposed receiving pads 16 with radially extending holes 27 the electrode rings aligned with the pads for future laser welding of the rings to the pads as depicted in FIGS. 14A-C. In these regards, after the manual positioning of the platinum rings 26 onto the pads 16, the tooling bow 46 is placed into a standard laser welding machine (not shown) where each electrode ring 26 and hole 27 is located by the laser vision system of the laser welding machine. The laser will then weld each ring 26 to each pad 16 at its ring hole 27 and the process repeated until all of the electrodes are welded in place.

After laser welding the electrodes 26, the wrapped electrode subassembly is plasma etched and the preformed microcircuit 12 placed into overmolding mold tooling. A section 49 of the wrapped electrode up to a first inactive visual electrode and the underside of the head portion 18 shown in FIG. 15 are then encapsulated with a silicone film 50 (comprising the overmolded plastic material 28) by overmolding apparatus such as described and illustrated in FIG. 9. The overmolding of the underside of the head portion 18 acts as reinforcing for the interconnect circuit and pads 20 and creates a stand-off that may be used for height referencing when attaching the microcircuit 12 to posts 52 extending vertically from a titanium housing 54 as shown in FIGS. 20 A and 20B.

After pre-curing the overmold section 49 shown in FIG. 15, the tooling bow 46 is mounted in overmold tooling and placed in overmold apparatus such as described and illustrated in FIG. 9. A section 60 of the wrapped microcircuit 12 shown in FIG. 16 between the overmold of FIG. 15 and the microcircuit section including the spaced ring electrodes is then encapsulated in a silicone film 56 depicted in FIG. 16. In this regard, the film 56 in section 60 is feathered down in size creating a smaller diameter of about 0.025 inches approximately 0.80 inches from the first inactive visual platinum electrode shown in FIG. 15.

After pre-curing the overmold film 56, the preformed and overmolded electrode is removed from the tooling bow 46. As shown most clearly in the enlarged view of FIG. 17B as well as in FIG. 17A, the electrode is then unwrapped at a junction 58 with section 60 including the spaced ring electrodes, offsetting the electrode section 60 including the spaced ring electrodes and creating a stylet lumen 62. A stylet 64 is inserted in the lumen 62 as illustrated in FIGS. 18A and 18B to straighten the electrode section 60 and the electrode and stylet are placed in an overmold apparatus similar to that shown and described relative to FIG. 9 where a silicone film 61 is formed encapsulating the electrode section 60. The completed electrode is then placed in a post-curing oven for final curing of the completed electrode assembly.

When the stylet 64 is removed from the lumen 62, the electrode section will assume the spiral shape shown in FIG. 17A. When it is desired to implant the electrode assembly, the stylet 64 is re-inserted in the lumen 62 using a conventional stylet insertion tool 66 such as shown in FIG. 18A, FIG. 18B showing the insertion tool 66 rotated 90 degrees to illustrate the handle 67 of the tool.

FIG. 19 shows the completed helix electrode assembly 10 ready for attachment of its head portion 18 to the platinum feedthrough posts 52 of the titanium housing 54 as shown in FIGS. 20A and 20B where the microcircuit interconnect or attachment pads 20 are slit slightly during laser machining to make intimate contact with corresponding ones of the feedthrough posts for laser welding to the posts.

While a preferred embodiment of the cochlear electrode and a for its manufacture have been illustrated and described in detail above, it is appreciated that changes and modifications may be made in the illustrated embodiments without departing from the spirit of the invention. Accordingly, the scope of present invention is to be limited only by the terms of the following claims.

The invention claimed is:

1. A process for manufacturing a single microcircuit into an integrated cochlear electrode array, comprising:
   securing and supporting a nonconductive film substrate;
   attaching a metallic ribbon to a surface of the film substrate;
   machining a flat multiconductor microcircuit from the ribbon including
      (i) a flat elongated multiconductor tail portion with spaced outwardly exposed electrode receiving pads, and
      (ii) a flat multiconductor head portion connected to the tail portion and having spaced outwardly exposed attachment pads;
   laminating the flat microcircuit between the film substrate and an insulating cover;
   excising the laminated microcircuit from the film substrate with the electrode receiving pads exposed;
   wrapping the tail portion of the excised laminated microcircuit into a helix with the exposed electrode receiving pads wrapped around the insulating cover;
   mounting and electrically connecting the ring electrodes on and to the exposed electrode receiving pads; and
   overmolding the helix tail portion with a polymeric material to ready the microcircuit for cochlear implant.

2. The process of claim 1 wherein the step of excising the laminated microcircuit also exposes the electrode receiving pads.

3. The process of claim 1 wherein the step of overmolding also includes overmolding an underside of the head portion.

4. The process of claim 1 wherein the step of securing and supporting the film substrate includes tensioning the film substrate in both an X-axis direction and a Y-axis direction.

5. The process of claim 4 wherein the tensioned film substrate is attached to a carrier.

6. The process of claim 5 wherein the attachment of the film substrate to the carrier comprises:
   locating an open lower frame under the tensioned film substrate and imparting relative vertical movement between the lower frame and the film substrate until attachment means on the lower frame engage the film substrate, and
   installing an open top frame of the carrier on the film substrate over the lower frame.

7. The process of claim 6 further including trimming excess film substrate from the carrier.

8. The process of claim 1 wherein the attaching of the ribbon to the film substrate is proceeded by an etching of mating surfaces of the ribbon and film substrate followed by lowering of the ribbon onto the film substrate where pressure and heat are applied for thermal compression attachment of the ribbon to the film substrate.

9. The process of claim 1 wherein the machining of the flat multiconductor circuit from the ribbon is by laser cutting of the ribbon.

10. The process of claim 9 wherein the laser cutting is with light impulses of femtosecond time duration.

\* \* \* \* \*